United States Patent
Zhou et al.

(10) Patent No.: US 6,500,969 B1
(45) Date of Patent: Dec. 31, 2002

(54) INTEGRATED HYDROGEN PEROXIDE PRODUCTION AND ORGANIC CHEMICAL OXIDATION

(75) Inventors: Bing Zhou, Cranbury, NJ (US); Michael Rueter, Plymouth Meeting, PA (US)

(73) Assignee: Hydrocarbon Technologies, Inc., Lawrenceville, NJ (US)

( * ) Notice: Subject to any disclaimer, the term of this patent is extended or adjusted under 35 U.S.C. 154(b) by 0 days.

(21) Appl. No.: 10/014,068

(22) Filed: Dec. 11, 2001

Related U.S. Application Data

(63) Continuation-in-part of application No. 09/733,154, filed on Dec. 8, 2000.

(51) Int. Cl.[7] ................ C07D 301/12; C07D 301/06
(52) U.S. Cl. ............. 549/531; 549/518; 549/523
(58) Field of Search ................. 549/531, 518, 549/523

(56) References Cited

U.S. PATENT DOCUMENTS 6,090,858 A  *  7/2000  El-sayed 6,168,775 B1  *  1/2001  Zhou et al.

FOREIGN PATENT DOCUMENTS

EP    0864363 A1  *  9/1998

* cited by examiner

*Primary Examiner*—Ba K. Trinh
(74) *Attorney, Agent, or Firm*—Daniel M. Kennedy

(57) ABSTRACT

A process for producing oxidized organic chemical products from various organic chemical feedstocks utilizing as oxidant hydrogen peroxide (H2O2) produced by noble metal nanocatalysis with high selectivity at low hydrogen concentration. The organic chemical oxidation process step can optionally be carried out in situ concurrent with the production of hydrogen peroxide or in a two stage process. In the two stage process, the hydrogen peroxide intermediate is directly produced by noble metal nanocatalysis from hydrogen and oxygen feeds plus a suitable solvent in a first catalytic reaction step. An organic chemical feedstock and the hydrogen peroxide intermediate and solvent solution are fed into a second catalytic reactor to produce an oxidized organic chemical product.

22 Claims, 1 Drawing Sheet

INTEGRATED HYDROGEN PEROXIDE PRODUCTION AND ORGANIC CHEMICAL OXIDATION

CROSS-REFERENCE TO RELATED PENDING APPLICATIONS

This application is a continuation-in-part of U.S. patent application Ser. No. 09/733,154 filed Dec. 8, 2000, allowed.

FIELD OF THE INVENTION

The invention comprises a process for producing organic chemicals by selective oxidation where the selective oxidation reaction is conducted using porous particles comprising specially synthesized nanometer-sized crystallites of supported noble metal catalyst. Classes of chemical substrates which can be selectively oxidized by the process of the invention include alkanes, olefins, alcohols, aromatics, ketones, aldehydes as well as compounds containing mixed functionality and/or heteroatoms such as sulfur or nitrogen.

BACKGROUND OF THE INVENTION

Selective oxidation reactions are a major class of chemical transformations accounting for the production of a wide variety of important chemical products, including epoxides, hydroxylates, alcohols, carbonyl compounds, acids, glycols and glycol ethers, oximes, lactones, and oxygenated sulfur and nitrogen compounds such as sulfoxides, sulfones, nitrones, azo compounds, and other N-oxides. Normally, performing these transformations efficiently and economically requires that a catalyst be used which allows the reaction to occur at a sufficiently high rate (activity) and favors the formation of the desired products (selectivity). Frequently, these catalysts are based, at least in part, on the use of a noble metal constituent such as platinum, palladium, iridium, rhodium, ruthenium, gold, osmium, and the like. Noble metals tend to have favorable activity and selectivity toward desired oxidative reactions. The noble metal may be used as a soluble complex (homogeneous catalyst), but it is also frequently used as a heterogeneous catalyst with the noble metal deposited onto a porous support.

Commonly, selective oxidation reactions are performed utilizing oxygen as the oxidizing agent. However, producing purified oxygen is expensive, requiring large capital investment and operating costs. Also, processes using purified oxygen combined with organic chemical feedstocks may accidentally achieve gas compositions in the explosive range, thereby posing a serious safety hazard. In other cases, selective oxidation processes utilize air as the oxidizing agent. But a major economic problem associated with such processes utilizing air is handling the accompanying undesired large flow of nitrogen which substantially increases process costs. Such oxidation processes can also be prone to forming explosive gas mixtures. Oxidative processes using oxygen or air also tend to suffer from product selectivity problems related to overoxidation of the organic chemical feedstock, normally producing undesired carbon oxides (CO, CO2).

An attractive alternative to using oxygen or air as the oxidizing agent is the use of peroxidic compounds to provide the reactive oxygen needed for oxidative transformations. One common version is the use of organic hydroperoxides as oxidizing agents. These hydroperoxide compounds, typically generated by air- or O2-oxidation of suitable intermediates, are reacted with chemical feedstocks to form oxygenated products and organic by-products. However, these organic by-products represent a significant disadvantage for processes of this type because a large amount of organic material must be recovered, either for recycle or for sale as a secondary product. In some cases, the amount of this secondary product is greater than the amount of the primary oxygenated product, and is typically a less desirable product. For example, conventional production of propylene oxide also results in production of large amounts of styrene or tert-butyl alcohol co-products which typically must be marketed in economically unpredictable markets. Furthermore, processes involving organic hydroperoxide intermediates pose significant safety hazards. Generating hydroperoxides requires reactions of air with organic chemicals which may form explosive mixtures. Furthermore, organic peroxides can themselves be explosive, particularly if they are accidentally concentrated above a certain critical concentration level.

Instead of using organic peroxides, hydrogen peroxide is a known desirable oxidizing agent. The byproduct of oxidation reactions using hydrogen peroxide is typically water, a safe compound that can be easily recovered and reused or disposed. The amount of water on a weight basis is much less than the amount of organic by-product when organic hydroperoxides are used, and thereby represents significant savings in process costs. However, past attempts to develop selective chemical oxidation processes based on hydrogen peroxide have encountered significant difficulties. Conventional hydrogen peroxide production utilizes the anthraquinone process, wherein the anthraquinone is first hydrogenated to hydroanthraquinone and then autoxidized to release hydrogen peroxide and the anthraquinone for recycle. Hydrogen peroxide is generated at low concentrations in the solution, and very large flows of anthraquinone and anthrahydroquinone must be handled in order to produce the desired hydrogen peroxide product. Accordingly, such conventionally produced hydrogen peroxide is generally too expensive for commercial use as an oxidizing agent for selective chemical oxidation processes.

An important alternative to the use of organic peroxides for the oxidation of organic compounds is the generation of hydrogen peroxide directly by the noble metal catalyzed reaction of hydrogen and oxygen. This approach avoids the difficulty of the accompanying large flows of a working solution and can reduce the cost of hydrogen peroxide. The prior art includes a number of catalytic technologies which directly convert hydrogen and oxygen to hydrogen peroxide, but generally utilize a hydrogen/oxygen feed wherein the hydrogen concentration is greater than about 10 mol %. These hydrogen concentrations are well above the flammability limit of about 5 mol % for such mixtures and create a serious process hazard with added process costs and capital equipment costs required to mitigate the explosive hazard. At hydrogen feed concentrations below 5 mol %, the prior art catalysts are not sufficiently active and selective to generate hydrogen peroxide product at a reasonable rate.

Recently, an improved process for direct catalytic production of hydrogen peroxide utilizing an active supported phase-controlled noble metal catalyst has been disclosed in applicants' U.S. Pat. No. 6,168,775 B1, incorporated herein by reference in its entirety. Employing the catalyst and process taught in the '775 patent, the foregoing problems and limitations in the manufacture of hydrogen peroxide have been overcome. Advantageously, the '775 catalyst is highly active and produces hydrogen peroxide from hydrogen and oxygen with superior selectivity over the prior art processes. Of special importance, the process of the '775 patent converts hydrogen and oxygen to hydrogen peroxide with high selectivity wherein the process hydrogen concentration is well below its flammability limit.

Various oxidation processes for organic chemical feedstocks utilizing hydrogen peroxide are known. For example, U.S. Pat. No. 4,701,428 discloses hydroxylation of aromatic compounds and epoxidation of olefins such as propylene using a titanium silicalite catalyst. Also, U.S. Pat. Nos. 4,824,976; 4,937,216; 5,166,372; 5,214,168; and 5,912,367 all disclose epoxidation of various olefins including propylene using titanium silicalite catalyst. European Patent No. 978 316 A1 to Enichem describes a process for making propylene oxide, including a first step for direct synthesis of hydrogen peroxide using a Pd catalyst, and a second step for epoxidation of propylene to form propylene oxide using titanium silicalite (TS-1) catalyst. However, the best hydrogen peroxide product selectivity reported is only 86%, based on the amount of hydrogen converted. In the process second step, the best selectivity of propylene oxide formation is 97%, based on hydrogen peroxide conversion. Therefore, the best overall yield of propylene oxide that can be achieved is 83%, based on hydrogen feed. However, higher yields of oxidized organic products are much desired, particularly when considering the relatively high cost of the hydrogen feedstock which is required for the direct catalytic synthesis of hydrogen peroxide.

While noble metals are often the preferred catalysts for selective oxidation reactions, their use is hindered by several factors. For example, because noble metals are extremely active oxidation catalysts, they can often over-oxidize the substrate, forming unacceptably high levels of by-products such as carbon oxides (CO and CO2). Only certain noble metal active sites or crystal faces give acceptable noble metal selectivity towards the desired products, but conventional methods for fabricating noble metal catalysts will often expose a substantial fraction of other, undesired active sites. These undesired sites may catalyze the formation of undesired by-products.

For example, many oxidation processes involve inserting oxygen at the end of the oxidizable organic molecular structure or substrate or, as often described, at the alpha carbon of the substrates. The desirable oxidative active site of the noble metal catalyst will be those metal atoms exposed on the crystal face in 110 planes. The top layer of the face 110 has the noble metal atoms configured in line, thereby allowing the adsorbed oxidizable substrates to be oxidized only from each end. However, for the crystal face 100 and 111, the metal atoms are not just exposed in a linear position; there are many metal atoms adjacent to every side of the central active site. The 100 and 111 crystal faces allow the adsorbed oxidizable substrate to be in contact with the oxidative agent such as oxygen from all directions, not merely the alpha carbon direction. This results in oxidative cleavage of the substrate to carbon oxides. Thus, a highly selective catalyst should expose mainly the desirable face 110, whereby excessive oxidation of the organic substrate can be avoided.

U.S. patent '775 teaches that the exposition of noble metal crystal faces can be successfully controlled by using soluble polymers that form dispersible organo-metallic complexes with the noble metals in a solution which impregnates a nanometer-sized catalyst substrate with the noble metal. To produce nanometer-sized particles, the absorbed metal particle size is controlled by the polymer molecular weight used to form the metallo-organic complex. Since the particle size is determined by the number of the metal atoms it contains, by varying the polymer type and molecular weight the metal atom number in each particle is controlled; thus, a metal particle size in the nanometer range is produced having a controlled exposition for the catalytic reaction of hydrogen and oxygen to produce hydroperoxide.

Another problem related to noble metal catalysts is the very high cost of the noble metal. Generally, one tries to use the noble metal sparingly, but even so the cost of the noble metal itself can be a major factor in the economics of oxidation processes. In order to maximize the activity of the noble metal, extremely small metal crystallites are preferred. However, fabricating extremely small crystallites is difficult, and it is also difficult to prevent such crystallites from agglomerating to form larger particles.

Another difficulty related to the cost of noble metals is attrition. Especially when reactions are conducted in liquid medium, attrition of active metal from the catalyst will occur. Attrition rates of 5–10% per year or more are common in commercial practice. At the very high cost of noble metals, this represents a major loss of value.

SUMMARY OF THE INVENTION

The object of the present invention is to provide a method to selectively oxidize organic compounds in a process which overcomes the aforementioned problems extant in the processes of the prior art for the oxidation of organic compounds by peroxides, especially hydrogen peroxide. In particular, the objectives of the present invention include the realization of substantially superior selectivities for the oxidation of organic compounds in a system where the oxidation can be carried out safely in situ, i.e., in a single step concurrent with the production of hydrogen peroxide or, optionally, sequentially by selectively producing hydrogen peroxide followed by the oxidation of the organic compound in a second step or vessel. Either method enjoys the advantage of highly selective hydrogen peroxide formation wherein the hydrogen reactant is present at a concentration safely below its flammability limit of, typically, 5 mole percent. However, the processes can also be carried out effectively at hydrogen concentrations above 5 mole percent.

In particular, a process is disclosed for the oxidation of organic chemical(s) by hydrogen peroxide oxidizing agent produced in situ, hereinafter referred to as the in situ mode of the invention. The process comprises introducing feedstreams comprising a solvent, hydrogen and oxygen reactants and at least one oxidizable organic chemical into a vessel under oxidizing conditions in contact with nanometer-size crystals of supported particles of noble metal catalyst contained in the vessel and having the face of the noble metal crystals include expositions predominantly of the 110 and/or 220 type of crystal planes. Optionally, the in situ mode of the invention may include a second catalyst comprising an organic chemical(s) oxidation catalyst introduced into the reaction mixture. The second catalyst is preselected based on its activity to selectivity catalyze the hydrogen peroxide/organic chemical(s) oxidation reaction in the in situ system of the invention. In either configuration of the in situ process, the hydrogen and oxygen are substantially converted to the hydrogen peroxide oxidizing agent and the organic chemical(s) is oxidized in situ in contact with the hydrogen peroxide product. The oxidized organic chemical(s) product, catalyst(s), solvent, unconverted organic chemical(s), hydrogen and oxygen are separated and recovered.

The two-stage process, or two-stage mode, of the invention for the selective oxidation of organic chemical(s) feedstocks utilizing directly produced hydrogen peroxide intermediate as oxidant comprises feeding hydrogen and oxygen-containing gas together with a solvent into a first catalytic reactor containing nanometer-size crystals of supported particles of noble metal catalyst under oxidizing conditions maintained at 0–100° C. temperature and 300–3,000 psig pressure, whereby hydrogen peroxide intermediate is formed at hydrogen concentrations below the flammability limits of hydrogen. The catalyst contains nanometer-size crystallite particles of supported noble metal catalyst having the face of the noble metal crystals include expositions predominantly of the 110 and/or 220 type of crystal planes;

The organic chemical feedstock and solvent plus said hydrogen peroxide intermediate in an amount sufficient to comprise 1–30 wt. % are introduced into the reaction mixture in a second catalytic reactor containing a second catalyst, preferably comprising titanium silicalite, under oxidizing conditions of 0–150° C. temperature and 15–1,500 psi pressure. The chemical feedstock is oxidized to provide an oxidized organic chemical product which is separated and recovered As those skilled in the art will appreciate, the two-stage mode of the invention may be carried as batch or continuous operations.

DETAILED DESCRIPTION OF THE INVENTION

In order to overcome the problems set forth above, a process has been invented for the selective oxidation of various organic chemicals using a supported phase-controlled noble metal catalyst with stable nanometer-size crystallites. Due to the advantageous properties of the process and catalyst, selective oxidation can be safely conducted efficiently and economically, with high activity and selectivity of the desired oxidation products, Very little agglomeration or attrition of the noble metal components of the catalyst is experienced.

Figure 1:
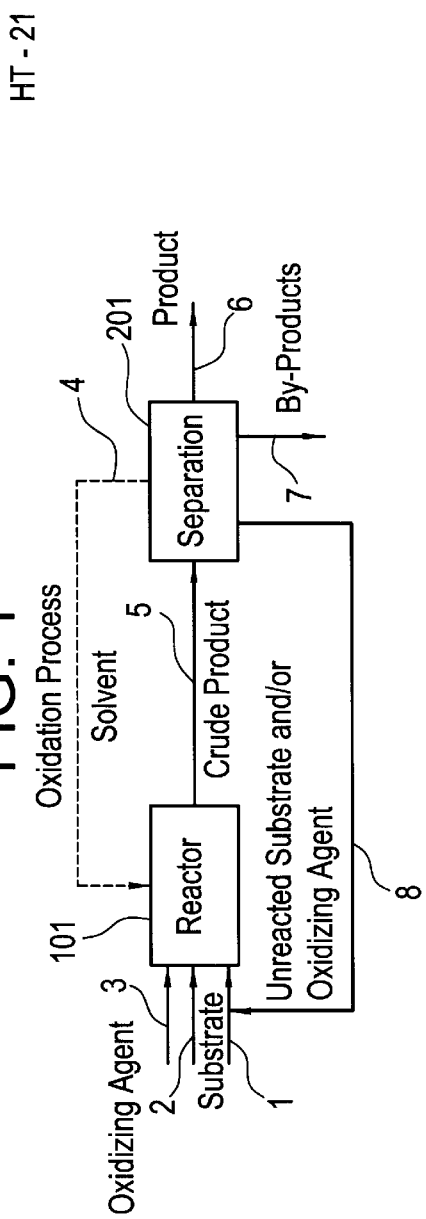
FIG. 1 is a block flow diagram of an optional in situ mode of the oxidation process of the invention.

The in-situ mode of the process of the invention is shown schematically in FIG. 1. In a suitably designed reactor(s) 101, an oxidizable organic chemical feedstream (1) is contacted with hydrogen and oxygen-containing feedstreams (2) and (3) in the presence of the supported, phase-controlled noble metal catalyst and, optionally, a second catalyst comprising an oxidation catalyst selective for organic chemical(s). A solvent (4) or reaction medium may also be fed, normally as a liquid. At oxidizing conditions maintained at 0–100° C. temperature and a pressure of 300–3,000 psig, hydrogen peroxide intermediate is catalytically formed in contact with the noble metal catalyst and the oxidizable organic chemical(s) is oxidized to the desired oxidation product. The effluent (5) from the reactor(s) is a crude oxidation product which contains the desired product or products, along with reaction by-products, unreacted substrate, solvent, and unreacted oxidizing agent. The crude oxidation product is subjected to a suitable separation process (201) to recover purified forms of the desired oxidation products (6), remove (7) the reaction by-products (which in some cases may also have commercial value), recover and recycle (8) unreacted substrate and solvent, and remove, vent, recycle, decompose, or otherwise handle unreacted oxidizing agent.

The phase-controlled noble metal catalyst used in the subject process is supported on a porous solid substrate (i.e. heterogeneous catalyst), so the reactor system used will be of an appropriate type. The optional second catalyst can be of the same or similar type (heterogeneous) but could also be a homogeneous catalyst. The reactor system can include fixed bed, moving bed, fluidized bed, slurry, loop, and other known types of heterogeneous catalytic reactors. Single or multiple reactors may be used. In the case of multiple reactors, these reactors can be arranged in series, parallel, or some combination, and may be all of the same type with the same catalyst, or may be of different types with different catalysts. Reactor operating conditions will depend on the specific substrate, product, catalyst, and oxidizing agent.

Generally, oxidation reactions conducted in the subject process will be exothermic. This may require use of heat removal equipment such as internal coils, jackets, shell-and-tube reactors, tube-in-tube reactors, external (pumparound) exchangers, preheaters, or intercoolers. Heat of reaction can also be removed by allowing a portion of the reacting mass to boil.

The process is conducted using a specially prepared phase-controlled supported noble metal catalyst from which the most important advantages of this process are derived. As noted herein before, the catalyst is described in detail in U.S. Pat. No. 6,168,775 B1. The catalyst consists of an inorganic oxide or carbon support deposited with nanometer-sized crystallites of one or more metal components, where the metal or metals normally include at least one noble (platinum-group) metal, especially palladium, in combination with one or more of platinum, rhenium, rhodium, ruthenium, osmium, iridium, gold, or combinations thereof. Other metal constituents such as nickel, tin, copper, iron, and the like, may be included either individually or in combination. The amount of noble metal constituents will typically be 0.1 to 5% of the total catalyst weight. Other components may also be included in amounts of 0.01 to 20% by weight, depending upon the selection and function of the additional component. The primary attribute of the noble metal catalyst employed in the invention is a capability to catalyze the direct formation of hydrogen peroxide from hydrogen and oxygen feedstreams with high selectivity, even at low, safe hydrogen concentrations.

The noble metal particles are deposited on carbon or inorganic metal oxide support. Examples of noble metal catalyst supports are activated carbon, carbon black, fluoridated carbon, alumina, bentonite, clay, diatomaceous earth, zeolite, silica, zirconia, magnesia, titania, and the like, and also mixtures of those. The support should preferably have a surface are of more than 20 m2/g, and more preferably more than 50 m2/g.

The noble metal crystallites are preferably deposited on the substrate using an ionic polymer binding agent which disperses the deposited metal into the desired nano-sized particles and bonds said particles to the surface very strongly. This controlled deposition method also allows metal crystallites to be deposited with a high selectivity towards specific metal crystal faces being exposed. These several features of the metal deposition method produce a catalyst with properties that are highly advantageous for use in the subject oxidation processes. By producing nanometer-sized particles, the method contributes to especially high catalyst activity. Controlled exposition of known metal crystal faces allows the selectivity of the catalytic reaction towards desirable products to be favored. The strong bonding of the metal crystallites to the substrate surface prevents later agglomeration of metal particles into larger structures, which would cause the desirable high activity of the catalyst to be lost. Further, the strong bonding substantially prevents the attrition of the active metal components into the surrounding liquid medium during use of the catalyst.

Oxidizing agents suitable for use in the subject process to produce hydrogen peroxide include preferably oxygen which may be introduced as a liquid or gaseous feedstream of purified oxygen, enriched air, or air. However, metallic and non-metallic oxygenates which may emit oxygen under the scope of the process conditions of the invention are recognized as falling within the spirit and scope of the instant invention.

Solvents which may be used in the processes of the invention include water, alcohols, ketones, aldehydes, ester, aromatics, nitrogen-containing compounds, and mixtures thereof. The preferred solvents include alcohols such as methanol and mixtures of alcohols and water.

The separation part of the process can include distillation, solvent extraction, absorption, adsorption, and other techniques known to those skilled in the art, applied either singly or in combination. In cases where higher value oxidizing agents such as purified oxygen or peroxides are used, any unreacted oxidizing may be recovered and reused in the reactor.

For the two stage mode of the process of the invention, the first stage involves the production of hydrogen peroxide from oxygen and hydrogen by noble metal catalysis. The second stage involves the catalyzed or non-catalyzed oxidation of the organic chemical(s) by hydrogen peroxide. Where a catalyzed oxidation is preferred, a wide variety of catalysts are useful for the second stage oxidation. Selection of the catalyst for the two stage mode oxidation step strongly depends on the type of organic chemical to be oxidized and the degree of oxidation, or selectivity, to be achieved.

When catalysis is elected, a particularly preferred catalyst for either the in situ mode or the two stage mode of organic chemical(s) oxidation of the process of the invention is titanium silicalite. However, zeolite-based materials, in general, are useful catalysts including variations on titanium-based zeolite catalysts containing other components such as tellurium, boron, germanium, and niobium; also, oxidation catalysts containing silicon (Si) and titanium (Ti) which are isomorphous with the structure of zeolite beta. Additional oxidation catalysts include titanium aluminophosphates (TAPO), chromium and iron incorporated silica aluminophosphates (SAPO), iron-substituted slicotungstates, zeolite-encapsulated vanadium picolinate peroxo complexes, and metal oxide ($TiO_2$, $MoO_3$, or $WO_3$) substituted silica xerogels. Organo-metallic complex based materials may also be employed including Zinc containing polyoxometalate, methyltrioxorhenium, and metalloporphyrin. Some heteropoly-compound based materials which may be used include molybdenum-vanadium-phosphate compounds and chromiun-containing heteropolytungstates.

Some catalysts useful for the complete or intermediate oxidation of organic chemicals in the two stage or in situ mode of the invention include those described in U.S. Pat. Nos. 5,679,749, 6,042,807, and 5,977,009 which U.S. Pat. Nos. 5,374,747, 5,412,122, 5,527,520, 5,554,356, 5,621,122, 5,684,170, and 5,695,736.

In either the single stage in situ mode of the invention or in the two stage mode, a wide variety of chemical products as shown in Table 1 can be produced using the subject process, starting from a variety of chemical species.

Figure 2:
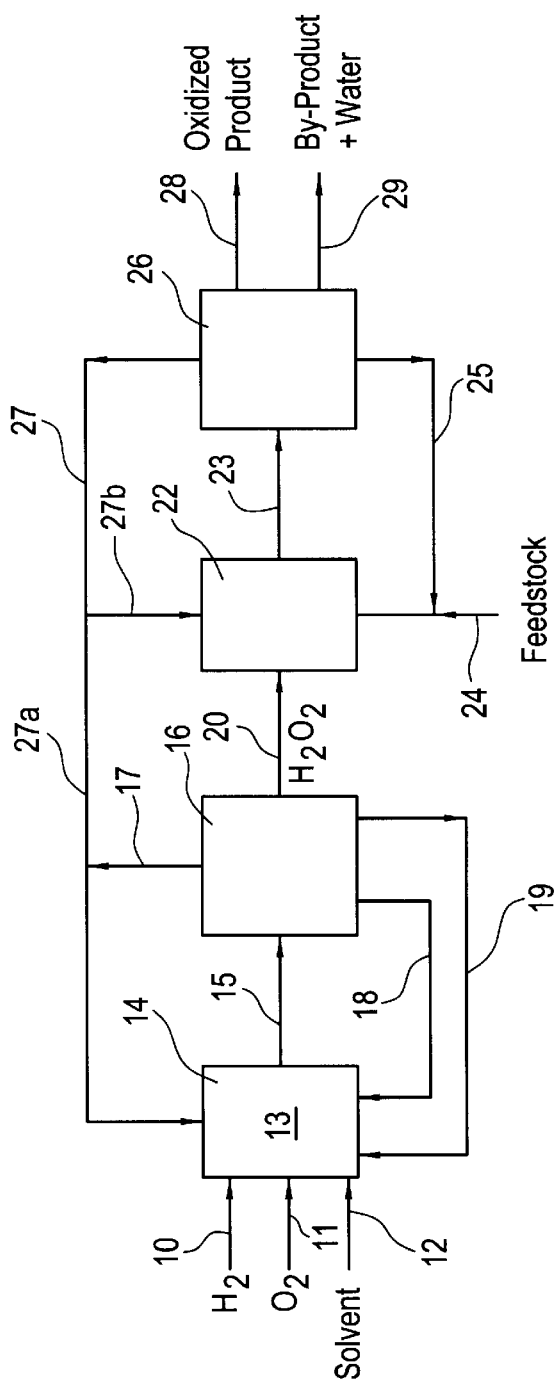
FIG. 2 is a process flow diagram for the two stage process of the invention.

In the alternate two stage mode of the instant invention the hydrogen peroxide direct production step and the selective oxidation reaction step for the organic chemical feedstock are performed in two separate reactors, with the general overall process being shown schematically in FIG. 2. In this process, hydrogen provided at 10 and oxygen (as purified oxygen or air) provided at 11 and with a liquid solvent 12 are reacted over the supported phase-controlled noble metal catalyst 13 in reactor 14 to generate a liquid solution of hydrogen peroxide intermediate product at 15. The reactor 14 may contain a fixed, fluidized or slurried bed of the catalyst 13 with a slurried catalyst bed usually being preferred. The liquid medium at 12 may be water, or it may be a suitable organic solvent such as alcohols or mixtures thereof. Suitable organic solvents can include various alcohols, aldehydes, aromatics, esters and ketones or other solvents compatible with the oxidizable organic compounds and their products depicted in Table 1. However, preferably solvents are water-soluble alcohols such as methanol, ethanol, isopropanol and mixtures thereof. The hydrogen concentration in reactor 14 is maintained below the flammability limit of about 5 mol %. The liquid-phase concentration of hydrogen peroxide intermediate product at 15 can vary over a useful range of 1–30 wt. %. A lower liquid phase peroxide concentration (e.g. <10 wt %) favors a high hydrogen selectivity of almost 100%, whereas a higher liquid phase peroxide concentration will favor reduced separation costs in downstream processing equipment. The optimum hydrogen peroxide concentration at 15 will depend on a variety of factors, including hydrogen cost, separation requirements, and optimal peroxide concentration for best performance of the downstream second-stage reactor. In general, the preferred H2O2 concentration at 15 will be 1–20 wt. %, and more preferably will be 2–15 wt. %.

The catalyst 13 for the first step direct catalytic production of the hydrogen peroxide intermediate from hydrogen and oxygen feeds in reactor 14 is a supported phase-controlled palladium (Pd) and platinum (Pt) slurry catalyst that selectively produces essentially only the hydrogen peroxide intermediate, as disclosed in applicants' U.S. Pat. No. 6,168,775 B1. By using appropriate ratios of an ionic linear polymer agent for making the catalyst, the noble metal atoms such as Pd are deposited on the support in a generally linear pattern that corresponds to forming mainly Pd crystal phase or face 110. Such Pd crystal phase exposition allows only limited hydrogen adsorbing on the adjacent metal sites that adsorb oxygen, avoiding the oxygen attached by more than enough hydrogen such as for Pd phases 100 and 111. The supported phase-controlled Pd catalyst has been experimentally proved to directly produce hydrogen peroxide at very high selectively. By using this catalyst in reactor 14 and at reaction conditions of 0–80° C. temperature and 500–3,000 psig pressure, the process first reaction step will produce hydrogen peroxide intermediate at selectivity near 100%.

While water may be used as the reaction medium at 12 for producing the hydrogen peroxide intermediate, it has been unexpectedly found that a significant advantage occurs with use of a water-miscible alcohol for at least part of the reaction solution mixture. Such alcohol usage significantly increases the rate of hydrogen peroxide formation in the first reactor 14, raising the productivity of the hydrogen peroxide producing reactor on a unit-catalyst basis. While alcohols have been used as solvent for direct H2O2 production in the prior art, no significant advantage for production rates have been reported. The combination of utilizing the phase-controlled noble metal catalyst of this invention with an alcohol or alcohol-water reaction medium provides a synergistic effect, yielding greatly improved performance relative to that disclosed by the prior art processes.

From the first step reactor 14, the effluent stream 15 is a mixture of hydrogen peroxide solution in water and/or alcohol and unreacted gases. As shown by FIG. 2, a separation step 16 may be provided between the first and second stage reactors. Generally, unreacted gases will be removed at 16 and after suitable scrubbing may be vented from the process, or in the case of purified oxygen feed at 12 the unreacted gases may be recycled at 18 back to the first reactor 14 to utilize the additional oxygen. Other than unreacted gas removal and possible catalyst recovery at 19 for reuse in reactor 14, this selective oxidation process configuration requires no further separations at 16 after the catalytic reaction stage 14. Although not preferred, in some cases it may be desirable to remove a portion of the solvent or water from the first reactor effluent at 17 to generate a suitable hydrogen peroxide feed concentration for the second stage reactor. From separation step 16, the hydrogen peroxide intermediate together with the remaining alcohol and/or water solution at 20 is passed on to a second catalytic reaction step at 22 for oxidation reaction with a selected organic chemical feedstock such as propylene provided at 24. The hydrogen peroxide concentration in stream 20 will preferably be the same as in the stream 15 from catalytic reactor 14.

In the second stage reactor 22, the hydrogen peroxide intermediate is reacted with the organic chemical feedstock 24 such as propylene to generate a desired crude organic product such as propylene oxide. This second reaction may be non-catalytic, but is usually based on a heterogeneous catalyst, possibly a zeolitic catalyst such as titanium silicalite or related catalysts, or based on a homogeneous catalyst. Depending upon the chemical feedstock provided at 24, the choice of selective oxidation catalyst will vary and suitable oxidation catalysts are known and described in the prior art. In cases where the second catalytic reactor contains a solid heterogeneous catalyst, various reactor types may be utilized, such as fixed bed, fluidized bed, slurry bed and other types known in the art. The optimal reactor choice will depend on several factors, including mass transfer, catalyst recovery cost, temperature control, and catalyst life and cost. The solvent used for this second reaction step 22 may be the same or different from that used in the first reactor 14 for making the hydrogen peroxide intermediate. However, use of the same solvent or reacting medium in both reactors 14 and 22 is preferred, thereby avoiding undesired separation steps at 16 between the two reactors. Suitable broad reaction conditions for reactor 22 are 0–150° C. temperature and 15–1,500 psig pressure, with 10–100° C. temperature and 50–1,000 psig pressure usually being preferred. The selection of the preferred reaction conditions will depend on the nature of the organic chemical feedstock.

After the selective oxidation reaction second step at reactor 22, the crude reaction product at 23 is subjected to one or more separations and/or distillations at 26 as needed to generate a purified oxidized chemical product, recover any unreacted feedstock or hydrogen peroxide at 25 and solvent at 27 for recycle, and remove water and other undesired by-products. If the same solvent solution is utilized for both reactor stages 14 and 22, with little or no separation in between the reactors as is preferred, then the solvent recovered at 26 will be recycled at 27 and 27a back to the first reactor 14. If the solvents are different, or if no solvent is used in the first stage reactor 14, then the solvent recovered at 26 from the second stage reactor 22 will be recycled at 27b back to the second stage reactor 22. The purified oxidized product is removed at 28 and by-products including water are removed at 29.

For the selective oxidation process of this invention, a large variety of selected organic chemical feedstocks may be provided at 24 to the second stage reactor 22, and reacted with the hydrogen peroxide intermediate at 20 which is produced directly from the hydrogen and oxygen feeds using the active supported phase-controlled noble metal catalyst 13, and then the hydrogen peroxide intermediate and catalysts known in the art used to selectively oxidize the various organic chemical feedstocks provided at 24 to produce important desired oxidized organic chemical products.

The above described product separation/distillation sequence of FIG. 2 is generally preferred, in that lighter products are removed first at higher pressure, followed by removal of heavier products at successively lower pressure. This scheme avoids excessively high temperatures in the bottom of any of the distillation towers, thereby preventing excessive decomposition of the product. However, other useful process schemes or sequences for oxidized product purification and recovery are also possible as will be understood by those skilled in this art, and it is understood that this process sequence per FIG. 2 is not meant to limit the scope of this invention.

The following Examples 1 and 2 are provided to illustrate the application of the In situ oxidation mode of the process of the invention (Example 1) and the two stage oxidation mode of the process of the invention (Example 2).

EXAMPLE 1

The In-situ Hydrogen Peroxide Oxidation Process 0.086 grams (g) of titanium silicalite-1 (TS-1), 0.23 g of a powdered palladium (Pd)-on-carbon nanocatalyst produced according to applicants' U.S. Pat. No. 6,168,775B1 and containing 0.7 weight percent Pd, and 50 g of methanol are charged to a reactor equipped with a stirring mechanism. The reactor is then pressurized with 32 g of propylene and raised to controlled conditions of 1400 psig pressure and 45° C. temperature. The liquid feed and solid catalyst mixture is agitated to form a well-mixed slurry. Into this slurry are continuously fed hydrogen gas at 0.1 mol/hr and oxygen at 3.3 mol/hr, which is an average feed concentration of 3 mol % hydrogen based on total gas feed. This concentration is below the lower flammable limit of a hydrogen/oxygen mixture and, therefore, a safe composition.

Under the foregoing conditions hydrogen peroxide is produced in situ by the reaction of hydrogen and oxygen on the Pd/C nanocatalyst. Unreacted gases are continuously withdrawn from the reactor through a pressure control valve which maintains the desired reactor pressure. The resulting hydrogen peroxide intermediate is than converted by reaction with propylene on the TS-1 catalyst into propylene oxide. After completion of a 4 hr reaction period, 84.5 g of liquid is withdrawn from the reactor and found to consist of 4.7 weight percent propylene oxide, 59 wt % methanol, 15.7 wt % propylene, and 1.5 wt % water. Small amounts of nonselective products including propylene glycol, methyl ethers of propylene glycol and propylene glycol oligomers are also produced.

Overall, the process produces propylene oxide at a selectivity of 90%, based on the moles of propylene converted. In situ generated hydrogen peroxide is generated at a selectivity of 95%, based on the moles of hydrogen converted. The hydrogen peroxide is then converted to propylene oxide at a selectivity of 90%, based on the moles of hydrogen peroxide converted. Propylene is reacted at a conversion of 10% and hydrogen is reacted at a conversion of 20%.

EXAMPLE 2

The Two-stage Hydrogen Peroxide Oxidation Process 0.23 g of a powdered palladium (Pd)-on-carbon nanocatalyst produced according to applicants' U.S. Pat. No. 6,168,775B1 and containing 0.7 weight percent Pd is charged to a reactor equipped with a stirring mechanism. 50 g of methanol are charged to the reactor. The liquid feed and solid catalyst mixture are agitated to form a well-mixed slurry. Into this slurry are continuously fed hydrogen gas at 0.1 mol/hr and oxygen at 3.3 mol/hr, which is an average feed concentration of 3 mol % hydrogen based on total gas feed. This concentration is below the lower flammable limit of a hydrogen/oxygen mixture and, therefore, a safe composition. The reactor is then controlled at conditions of 1400 psig pressure and 45° C. temperature.

Under the foregoing conditions hydrogen peroxide is produced in the liquid solution by the reaction of hydrogen and oxygen on the Pd/C nanocatalyst. Unreacted gases are continuously withdrawn from the reactor through a pressure control valve which maintains the desired reactor pressure. After completion of a 4 hr reaction period, the gas feeds are stopped and the liquid product is withdrawn from the reactor. After removal of the Pd/C nanocatalyst by filtration, the liquid solution is found to contain 5 wt % of hydrogen peroxide.

In this first reaction step, 20% of the hydrogen fed to the reactor is converted. Hydrogen peroxide intermediate is generated by the catalytic reaction on Pd/C nanocatalyst at a selectivity of 95%, based on the moles of hydrogen converted.

In a second reactor, 0.086 g of titanium silicalite-1 (TS-1) catalyst is provided in a powdered form suitable for suspension as a slurry. The peroxide-containing intermediate liquid solution obtained from the first reaction step is charged as liquid feed for the second step reaction. The second reactor is then pressurized with 16 g of propylene. The reactor is raised to a controlled pressure of 300 psig and a temperature of 45° C. Under these conditions hydrogen peroxide and propylene react over TS-1 catalyst to form propylene oxide.

After completion of a 4 hr reaction period, 84.5 g of liquid is withdrawn from the reactor and found to consist of 4.7 weight percent propylene oxide, 59 wt % methanol, 15.7 wt % propylene, and 1.5 wt % water. Small amounts of non-selective products including propylene glycol, methyl ethers of propylene glycol and propylene glycol oligomers are also produced.

20 wt % of the total propylene fed to the second step reaction is converted. Propylene oxide is generated by the second step catalytic reaction at a selectivity of 90%, based on the moles of hydrogen peroxide converted and 90% based on the moles of propylene converted.

TABLE 1

USEFUL PRODUCTS AND SUBSTRATES OF THE INVENTION
Possible Oxidation Reactions Using Phase-Controlled Noble Metal Catalyst

| Reaction | Product | Substrate | Specific Examples |
|---|---|---|---|
| General Oxidation Reactions | | | |
| | Carbonyls | Alkanes | Ethlyene -> Acetaldehyde |
| | | Olefins | |
| | | Alcohols | |
| | Carboxylic Acids | Olefins | Ethylene -> Acetic Acid |
| | | | Propylene -> Acrylic Acid |
| | | Alkanes | Cyclohexane -> Adipic Acid |
| | | Alcohols | |
| | | Carbonyls | Hydroxypivaldehyde -> |
| | | Sugars | Hydroxypivalic Acid |
| | | Unsaturated Fatty Acid | |
| | Alcohols | Alkanes | Methane -> Methanol |
| | | Olefins | |
| | Phenoxybenzoic Acids | Phenoxytoluenes | |
| Acetoxylation | Vinylic Ester of Carboxylic Acid | Olefin + Carboxylic Acid | Ethylene + Acetic Acid -> Vinyl Acetate |
| | Diols (glycols) | Olefins | Metyhacrylic Acid -> Methylglyceric Acid |
| | Glycol Ethers | Olefin + Alcohol | MeOH + Propylene -> PG Methyl Ether |
| | Esters or Alcohols + Carboxylic Acids | | Linear Ketones Unsaturated Fatty Acid Ester |
| | Oximes | Carbonyls | Cyclohexanone -> Cyclohexanone Oxime |
| | Lactones or Hydroxy acids Oxindoles | Cyclic Ketones Indoles | Cyclohexanone -> Caprolactone |
| | Heterocyclic N-oxides Nitrones Azo Compounds Sulfoxide or Sulfone | Nitrogen Heterocycles Secondary Amines Hydrazo Compounds Sulfide | Pyridine -> Pyridine N-Oxide |
| Epoxidation | | | |
| | Epoxides | Olefins | Ethylene -> Ethylene Oxide |
| | | | Propylene -> Propylene Oxide |
| | | | Cyclooctene -> Cyclooctene Oxide |
| | | | Styrene -> Styrene Oxide |
| | | | Stilbene -> Stilbene Oxide |
| | | | Cyclohexene -> Cyclohexene Oxide |
| | | | Cyclo pentene -> Cyclopentene Oxide |
| | | | Norbornene -> Norbornene Oxide |

What is claimed is:

1. A process for the oxidation of organic chemical(s) by hydrogen peroxide oxidizing agent produced in situ, the process comprising:

introducing feedstreams comprising a solvent, hydrogen and oxygen reactants and at least one oxidizable organic chemical into a vessel under oxidizing conditions in contact with nanometer-size crystals of supported noble metal catalyst contained in the vessel and having the face of the noble metal crystals include expositions predominantly of the 110 and/or 220 type of crystal planes, wherein the hydrogen and oxygen are substantially converted to the hydrogen peroxide oxidizing agent and the organic chemical(s) is oxidized in situ in contact with the hydrogen peroxide product; and separating the process products and recovering the separated oxidized organic chemical(s) product, catalyst, solvent, unconverted organic chemical(s), hydrogen and oxygen.

2. The process of claim 1 further including a second catalyst comprising an organic chemical(s) oxidation catalyst selected from the group consisting of titanium silicalite, titanium-based zeolite catalysts containing one or more of tellurium, boron, germanium, and niobium; catalysts containing silicon (Si) and titanium (Ti) which are isomorphous with the structure of zeolite beta, titanium aluminophosphates (TAPO), chromium and iron incorporated silica aluminophosphates (SAPO), iron-substituted silicotungstates, zeolite-encapsulated vanadium picolinate peroxo complexes, metal oxides including TiO2, MoO3, WO3 and substituted silica xerogels, zinc-containing polyoxometalate, methyltrioxorhenium, metalloporphyrin, molybdenum-vanadium-phosphate compounds and chromium-containing heteropolytungstates.

3. The process of claim 1 wherein one or more of the recovered catalyst, solvent, unconverted organic chemical (s), hydrogen and oxygen are recycled to the vessel.

4. The process of claim 1 wherein the solvent includes water, alcohols, ketones, aldehydes, esters, aromatics, nitrogen-containing compounds and mixtures thereof.

5. The process of claim 4 wherein the solvent preferably comprises alcohols.

6. The process of claim 1 wherein said oxygen includes air and oxygen-enriched air.

7. The process of claim 1 wherein the concentration of hydrogen introduced into the vessel is maintained below the flammability limit of hydrogen of less than 5 mole percent.

8. The process of claim 1 wherein the concentration of hydrogen introduced into the vessel is maintained above 5 mole percent.

9. The process of claim 1 wherein the noble metal catalyst includes palladium, platinum, gold, iridium, osmium, rhodium, or ruthenium, and combinations thereof deposited on a particulate support material to contain 0.01–10 wt. % of the noble metal and having a total surface area of 20–1500 m2/ gm.

10. The process of claim 9 wherein the noble metal catalyst comprises a mixture of palladium and platinum.

11. The process of claim 1 wherein the oxidizing conditions comprise 0–100° C. temperature and 50–3,000 psig pressure.

12. The process of claim 1 wherein said oxidizable organic chemical(s) is selected from the group consisting of alkanes, alkenes including haloalkenes, alcohols including olefinically unsaturated alcohols, carbonyls including alicyclic ketones, aromatic chemicals, unsaturated carboxylic acids and esters including unsaturated fatty acids, sugars, aromatic chemicals including substituted aromatics, aromatic and aliphatic nitrogen compounds, oxygen and sulfur heterocyclics, amino compounds, aliphatic sulfides, hydrazo compounds and unsaturated polymers.

13. The process of claim 1 wherein the oxidized product produced includes carbonyls, carboxylic acids, alcohols, organosulfoxides, nitrogen oxides, epoxides and hydroxylated aromatics.

14. A two-stage process for the selective oxidation of organic chemical(s) feedstocks utilizing directly produced hydrogen peroxide intermediate as oxidant, the process comprising:

feeding hydrogen and oxygen-containing gas together with a solvent into a first catalytic reactor containing a first particular supported phase-controlled noble metal catalyst under oxidizing conditions wherein hydrogen peroxide intermediate is formed, said catalyst containing nanometer-size particles of supported crystals of noble metal catalyst having the face of the noble metal crystals include expositions predominantly of the 110 and/or 220 type of crystal planes;

separating and recovering the hydroperoxide intermediate;

introducing an organic chemical feedstock and solvent plus said hydrogen peroxide intermediate in an amount sufficient to comprise 1–30 wt. % of the reaction mixture into a second catalytic reactor containing a second catalyst comprising an organic chemical(s) oxidation catalyst under oxidizing conditions, and oxidizing the chemical feedstock to provide an oxidized organic chemical product;

separating said second catalyst and unused solvent from the oxidized organic product; and recovering the oxidized organic chemical(s) product from the process.

15. The process of claim 14 wherein said first catalyst comprises a particulate support material having total surface area of 20–1500 m2/ gm; and 0.01–10 wt. % noble metal controllably deposited on said particulate support material, said noble metal having a wide distribution of minute crystals each having a size of 0.5–100 nanometers (nm) on said particulate support and has atoms of the noble metal exposed in an orderly linear alignment pattern on the metal crystals, so that at least most of the noble metal crystals have a phase exposition of 110 and/or 220, wherein said noble metal comprises palladium alone or in combination with one or more of platinum, gold, iridium, osmium, rhodium, and ruthenium.

16. The organic chemical selective oxidation process of claim 14 wherein said second catalyst is selected from the group consisting of titanium silicalite, titanium-based zeolite catalysts containing one or more of tellurium, boron, germanium, and niobium; catalysts containing silicon (Si) and titanium (Ti) which are isomorphous with the structure of zeolite beta, titanium aluminophosphates (TAPO), chromium and iron incorporated silica aluminophosphates (SAPO), iron-substituted silicotungstates, zeolite-encapsulated vanadium picolinate peroxo complexes, metal oxides including TiO2, MoO3, WO3 and substituted silica xerogels, zinc-containing polyoxometalate, methyltrioxorhenium, metalloporphyrin, molybdenum-vanadium-phosphate compounds and chromium-containing heteropolytungstates.

17. The process of claim 14 wherein said organic chemical(s) feedstock is selected from the group consisting of alkanes, alkenes including haloalkenes, alcohols including olefinically unsaturated alcohols, carbonyls including alicyclic ketones, aromatic chemicals, unsaturated carboxylic acids and esters including unsaturated fatty acids, sugars, aromatic chemicals including substituted aromatics, aromatic and aliphatic nitrogen compounds, oxygen and sulfur heterocyclics, amino compounds, aliphatic sulfides, hydrazo compounds and unsaturated polymers.

18. The process of claim 14 wherein the oxidized organic chemical(s) product produced includes carbonyls, carboxylic acids, alcohols, organosulfoxides, nitrogen oxides, epoxides and hydroxylated aromatics.

19. The process of claim 14 wherein the first reactor oxidizing conditions comprise temperature maintained at 0–100° C. temperature and pressure of 300–3,000 psig.

20. The process of claim 14 wherein the second reactor oxidizing conditions comprise temperature of 0–150° C. and pressure of 15–1,500 psi.

21. The process of claim 14 wherein the solvent includes water, alcohols, ketones, aldehydes, esters, aromatics, nitrogen-containing compounds and mixtures thereof.

22. The process of claim 14 wherein the separation of the hydrogen peroxide intermediate is carried out by solvent removal whereby a concentrated hydrogen peroxide intermediate feedstream is recovered and passed to the second stage reactor.

* * * * *